United States Patent [19]
Loebker et al.

[11] Patent Number: 5,307,839
[45] Date of Patent: May 3, 1994

[54] BOTTLED GAS CART

[76] Inventors: Kenneth L. Loebker; E. Larry Hicks, both of 1895-A Beaver Ruin Rd., Norcross, Ga. 30071

[21] Appl. No.: 937,690

[22] Filed: Sep. 1, 1992

[51] Int. Cl.$^5$ .............................................. A01G 25/09
[52] U.S. Cl. .................. 137/899; 137/382; 248/129
[58] Field of Search ............... 137/899, 382; 248/129; 239/172, 305

[56] References Cited

U.S. PATENT DOCUMENTS

| | | | |
|---|---|---|---|
| 1,326,768 | 12/1919 | Morgan | 137/382 |
| 1,424,846 | 8/1922 | Noyes | 137/382 |
| 1,715,538 | 6/1929 | Dean et al. | 137/382 |
| 1,738,096 | 12/1929 | Cole | 248/129 |
| 2,624,483 | 1/1953 | Ketzel | 248/129 |
| 3,797,744 | 3/1974 | Smith | 137/899 |
| 4,341,237 | 1/1982 | Stauffer | 137/883 |
| 4,708,162 | 11/1987 | Bayat | 137/382 |
| 4,864,344 | 9/1989 | Ellis | 248/129 |

*Primary Examiner*—A. Michael Chambers
*Attorney, Agent, or Firm*—Harris Zimmerman

[57] ABSTRACT

A movable cart for supporting pressurized gas cylinders in hospital operating rooms has a housing preferably proportioned to enclose a pair of cylinders in upright side by side positions. Wheels at the base of the housing are positioned to support the housing when it is tilted for transporting while enabling the housing to rest directly on the underlying surface when in a more upright orientation. A third wheel carried by a pivoting leg is swung outward from the base of the housing when it is to be tilted and moved. The housing may have a plurality of gas outlet fittings, a cylinder selector valve, plural pressure regulators for simultaneous delivery of different pressures and plural gauges for indicating pressures in different portions of the gas flow path. The cart provides a highly stable support base for the cylinders in both the upright orientation and the inclined traveling position, facilitates movement of the heavy cylinders, protects the cylinders from damage and simplifies hospital procedures which require a supply of compressed gas.

4 Claims, 5 Drawing Sheets

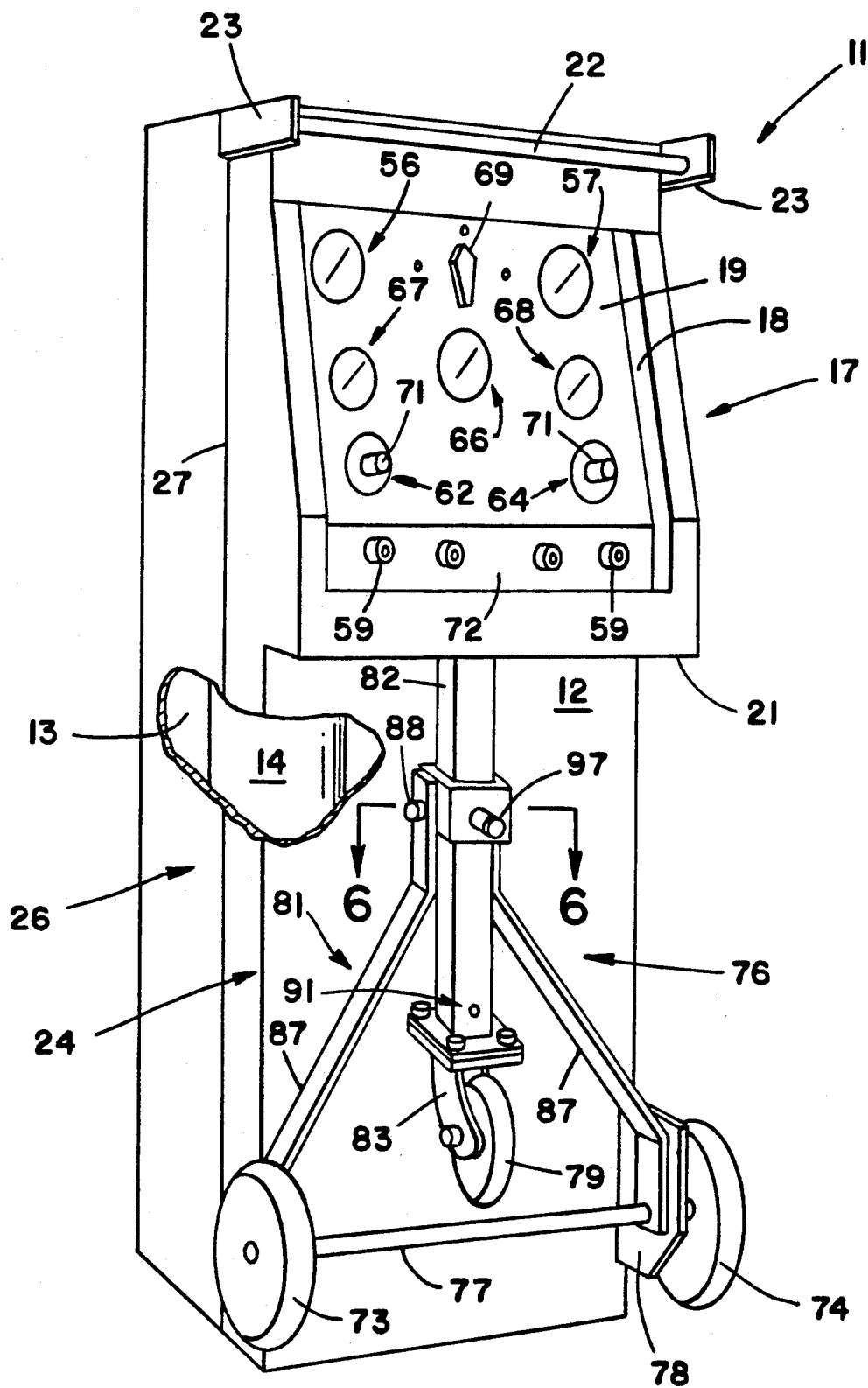
FIG_1

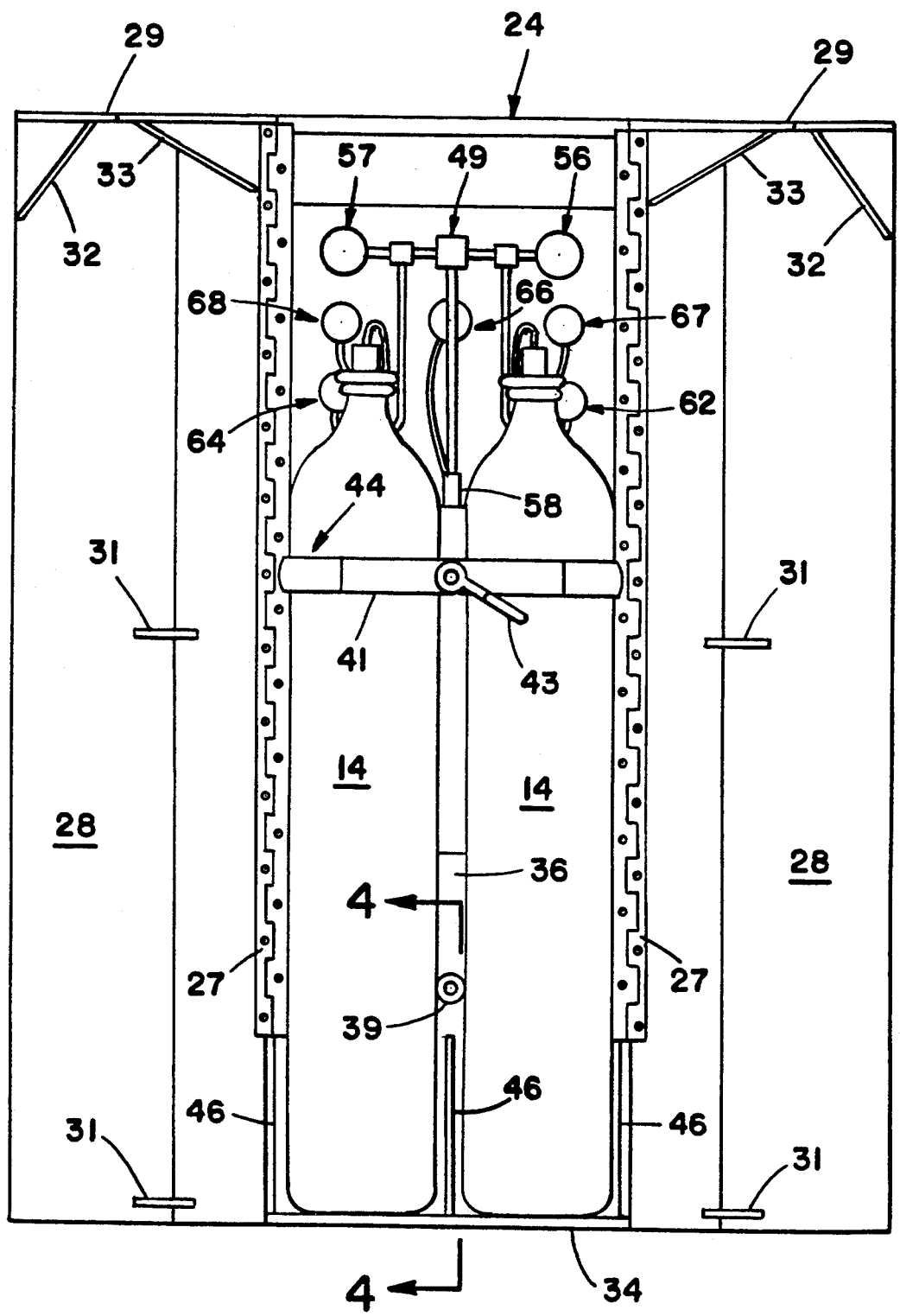
FIG_2

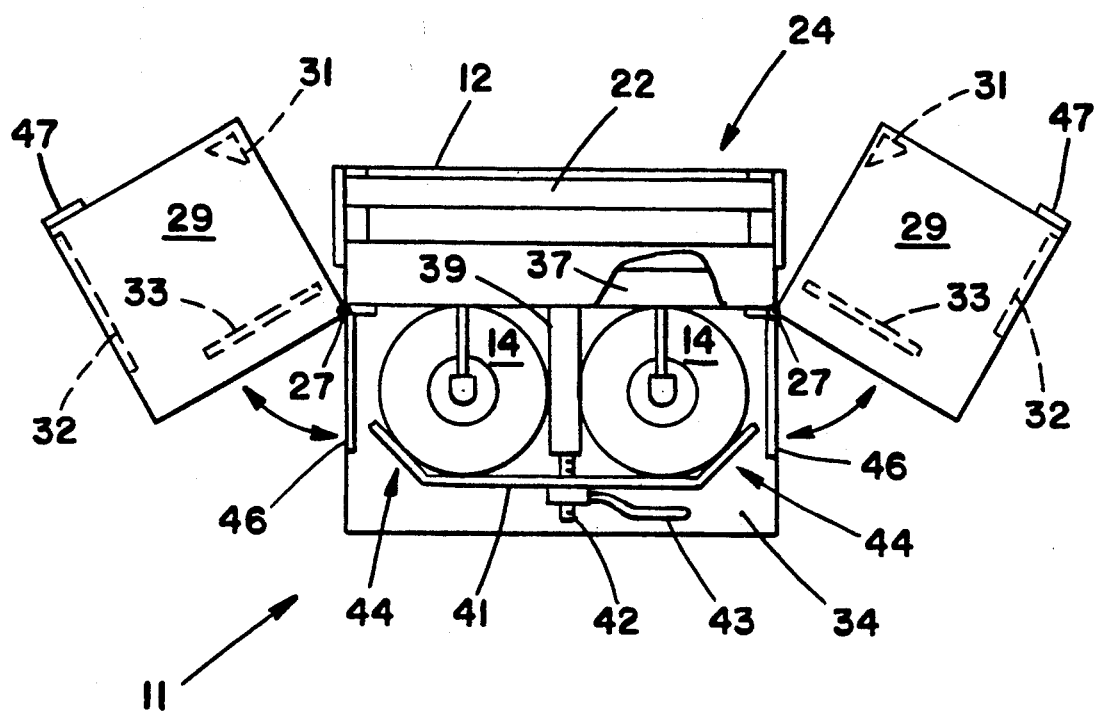
FIG_3
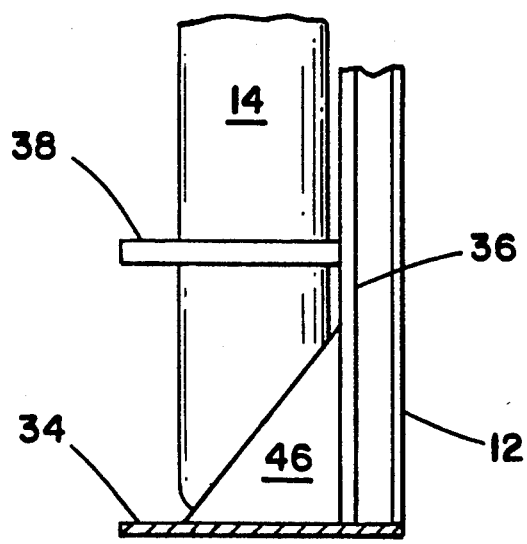
FIG_4

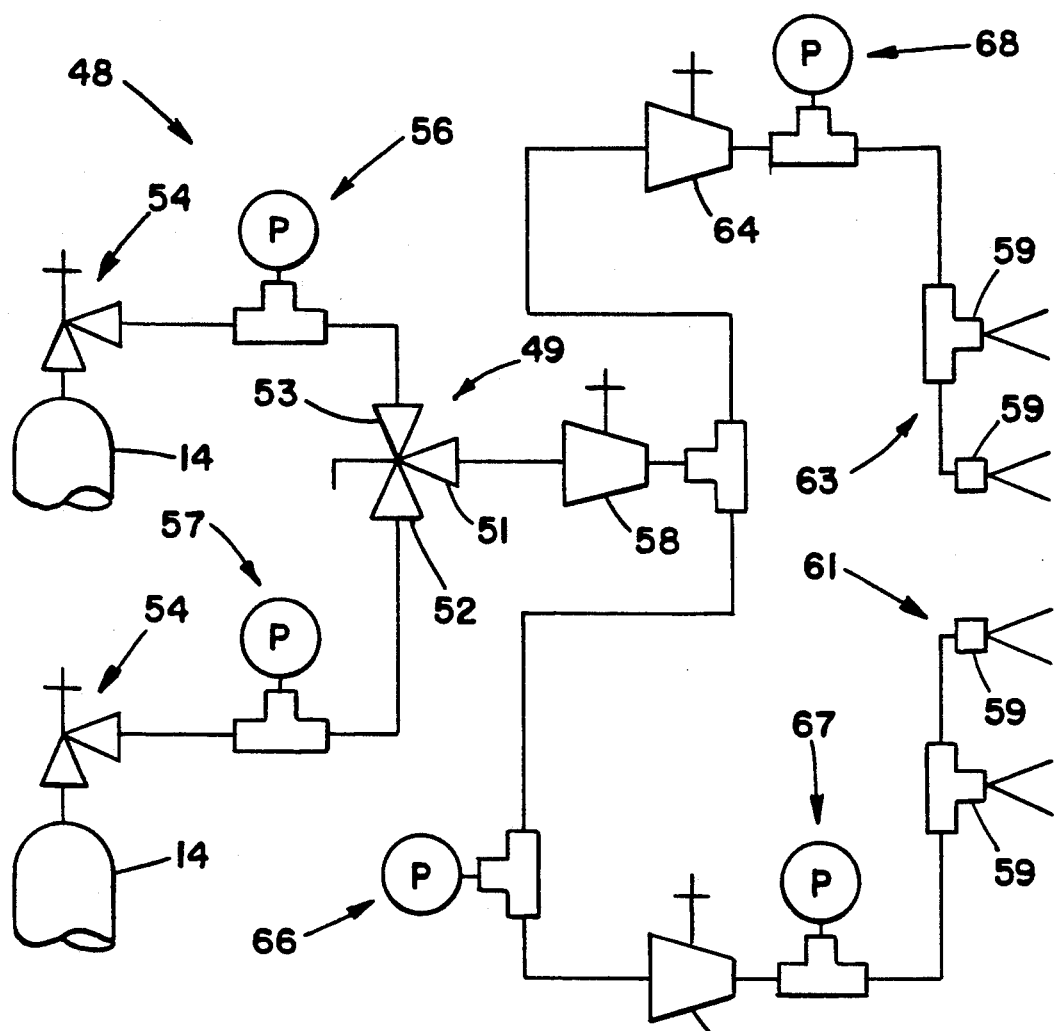
FIG_5
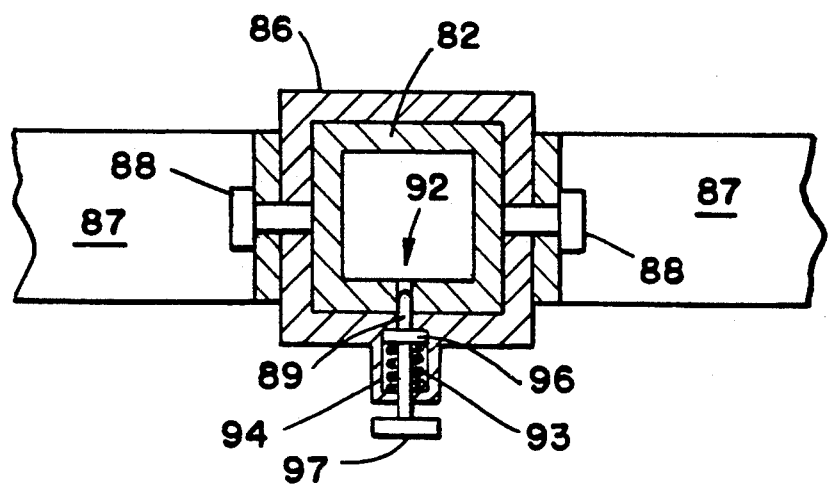
FIG_6

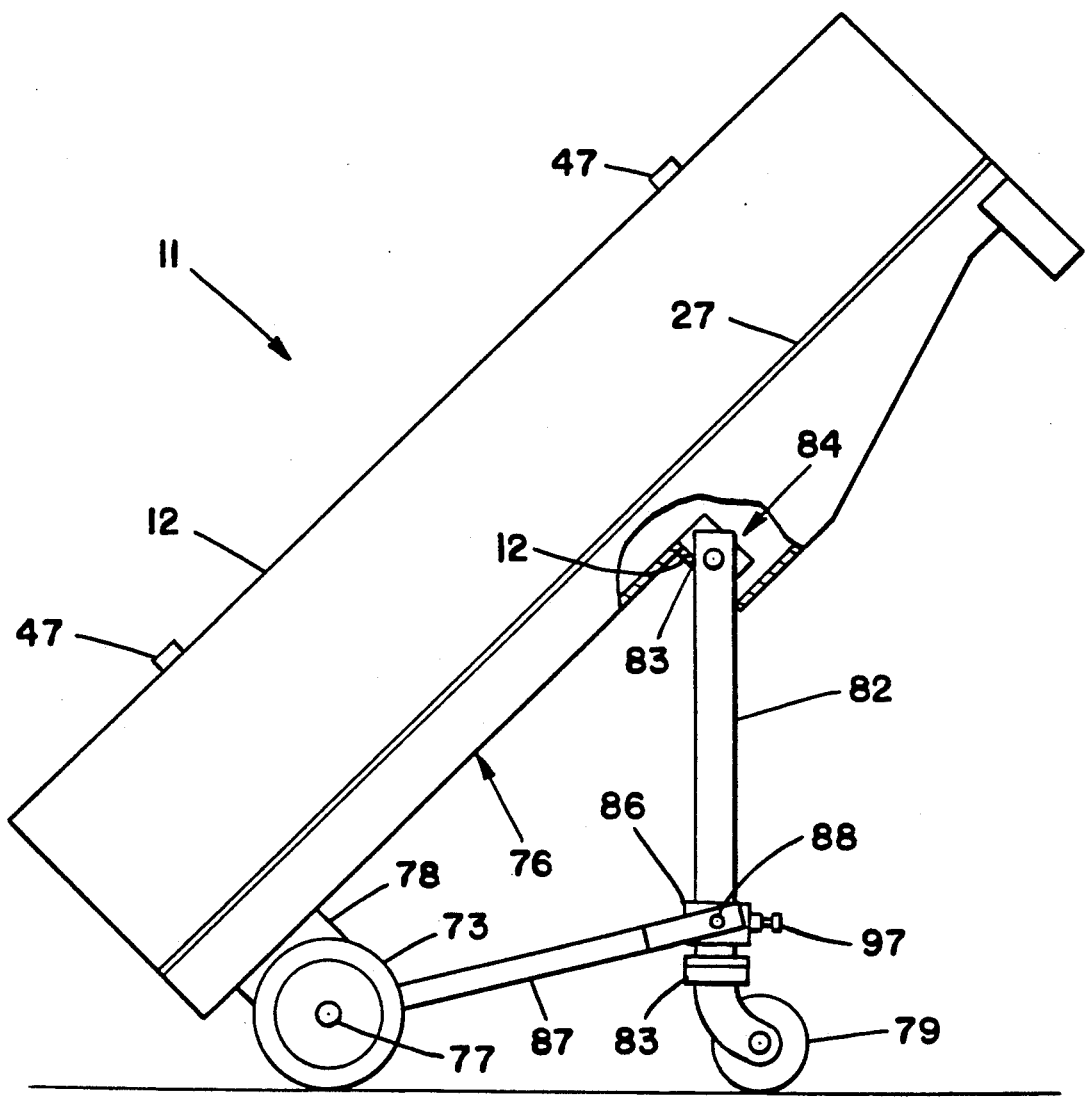
FIG_7

BOTTLED GAS CART

TECHNICAL FIELD

This invention relates to apparatus for supporting and moving cylinders of compressed gas and more particularly to wheeled carts which are used as gas cylinder carriers in hospital operating rooms or at other locations where bottled gases are utilized.

BACKGROUND OF THE INVENTION

Several forms of surgical tool are pneumatic devices that are operated by a flow of pressurized gas. Many hospitals have a piped in supply of compressed nitrogen gas but often the performance of pneumatic tools is adversely affected by inadequate pressure in the piping system of such gas supplies. Consequently, it is often necessary or at least advisable to have bottled gas available in the operating room or the like.

The bottles or gas cylinders are bulky and are formed of thick metal as sizable pressures of the order of 2750 psi for example, must be contained. This makes the gas cylinders heavy and difficult to carry. The cylinders also have a narrow, elongated configuration and thus cannot safely be rested on a floor or other surface in an upright position unless some additional support is provided.

These problems have heretofore been addressed by strapping the gas cylinder to a cart like carrier. Prior carriers of this kind have an open framework of tubular members that form a cradle for receiving the gas cylinder, the cradle and thus the cylinder being in an inclined orientation. Wheels at the underside of the carrier frame enable movement of the cylinder from one location to another and also continue to support the cylinder when it is at rest including at times when it is in use.

The prior carriers serve to support a gas cylinder and facilitate movement of the cylinder but do not otherwise resolve a number of problems associated with the use of high pressure gas cylinders in an operating room or the like. The prior carriers in fact create certain problems.

The prior carriers do not provide a desirably stable support base for the cylinder. The pressure regulator and pressure gauge which are customarily attached to the outlet of the cylinder are exposed to damage. Such damage can have very undesirable consequences as an uncontrolled outflow of the high pressure gas can propel objects about the room.

The inclined orientation of the cradle and cylinder causes carriers of the above described kind to occupy an undesirable amount of space in the often crowded operating room. The problem is compounded in that it is often desired to have two or more of the carriers in the room. Two or more cylinders may be needed to provide for simultaneous gas flows at different pressures for different tools or simply to provide assurance that the gas supply will not be exhausted in the course of a surgical procedure.

The prior carriers function only as a support for a gas cylinder and are not otherwise designed to facilitate the use of pneumatic tools in surgical procedures. For example, only one gas flow at one selected pressure is is available from a single carrier itself. Pressure regulators and gauges are mounted on the cylinder itself and can be somewhat difficult to read. Cleaning the convoluted surfaces of the carrier frame and cylinder in order to provide an aseptic environment in the operating room requires an undesirable amount of effort.

The present invention is directed to overcoming one or more of the problems discussed above.

SUMMARY OF THE INVENTION

In one aspect, the present invention provides a movable cart for supporting at least one pressurized gas cylinder. The apparatus includes a housing proportioned to receive and contain the cylinder and having means for selectively securing the cylinder at a fixed position within the housing and means for delivering a flow of gas from the cylinder to a location outside of the housing. First and second spaced apart wheels are journaled to the lower end of the housing, the wheels being at locations which cause the housing to be raised from the underlying floor and to be supported by the wheels when the housing is in a tilted orientation.

In another aspect of the invention, the first and second wheels are positioned to cause the housing to be supported by the floor independently of the wheels when the housing is upright.

In another aspect of the invention, the cart has a third wheel coupled to the housing by linkage means which enables selective positioning of the third wheel at a first location that is adjacent the housing and at a second location that is spaced outward from the housing.

In another aspect of the invention, the cart is proportioned to contain at least a pair of the cylinders and the means for delivering a flow of gas includes a plurality of gas flow outlet fittings secured to the housing, at least a pair of gas conduits adapted for coupling to separate ones of the cylinders, a cylinder selector valve having separate inlets coupled to separate ones of the conduits and an outlet for transmitting gas to the outlet fittings, a first pressure reducing pressure regulator forming a portion of the flow path from the valve to the outlet fittings, second and third manually adjustable pressure regulators each being connected between the valve and a separate group of the outlet fittings and a plurality of pressure gauges with pressure indicating means. A first gauge is coupled to one of the gas conduits and a second gauge is coupled to the other conduit. A third gauge is coupled to the outlet of the first pressure regulator. Fourth and fifth gauges are coupled to the outlets of the second and third pressure regulators.

In still another aspect of the invention, a movable cart for supporting and transporting pressurized gas cylinders has a housing forming a compartment of sufficient size to contain a pair of gas cylinders in upright side by side positions, a first portion of the housing walls being joined to another portion by hinges to enable opening of the housing. First and second wheels are journaled to the housing and are situated at the base of the front of the housing at opposite side regions of the housing. The wheels are positioned to extend forward from the base of the housing front wall and to extend upward from the plane of the housing floor at locations which cause the housing to be raised from the underlying surface and to be supported by the first and second wheels when the housing is tilted and which cause the housing to rest on the underlying surface when it is shifted to a more upright orientation. At least one pivotable leg is adjacent the front wall of the housing and has an upper end pivoted to the housing and a lower end that may be pivoted outward from the housing. The cart further includes means for selectively holding the leg at the outwardly pivoted position and a third wheel coupled to the lower end of the leg and which is swivelable. Further components which are secured the housing include a plurality of gas outlet fittings, a cylinder selector valve having a valve setting selector and means for transmitting gas from a selected one of the gas cylinders to the outlet fittings in response to actuation of the valve setting selector.

The invention is a mobile self contained pressurized gas supply cart which provides a highly stable and compact support base for gas cylinders and which protects the cylinders and other components of the gas system from damage. In the preferred form of the invention, the cart carries two cylinders in side by side relationship within an openable housing which is tilted and wholly supported by wheels when it is being moved and which is upright and rests directly on the floor when it is stationary. The preferred form of the invention has a plurality of gas outlet fittings enabling simultaneous operation of a number of pneumatic tools from the same gas cylinder and further enables simultaneous delivery of different gas flow pressures to different tools. The operator may switch from one gas cylinder to another by a simple control manipulation. Pressure selection controls and pressure indicators are built in components and can be clustered at the face of the gas cylinder housing at an easily accessible and easily viewed location. The housing may have smooth unconvoluted exterior surfaces which are easily cleaned to maintain an aseptic environment in the operating room.

The invention, together with further aspects and advantages thereof, may be further understood by reference to the following description of the preferred embodiment and by reference to the accompanying drawings.

BRIEF DESCRIPTION OF THE DRAWINGS

FIG. 1 is a frontal perspective view, partially broken out, of a bottled gas cart embodying the invention, the cart being shown in the upright orientation in which it is placed when the cart is stationary.

FIG. 2 is a rear view of the cart shown in an open condition which enables emplacement and removal of gas cylinders.

FIG. 3 is a top view of the opened cart of FIG. 2.

FIG. 4 is an elevation section view of the base region of the cart taken along line 4—4 of FIG. 2.

FIG. 5 is a schematic diagram of the gas flow system of the cart.

FIG. 6 is a cross section view taken along line 6—6 of FIG. 1 and depicting a portion of the wheel linkage of the cart.

FIG. 7 is a side view of the cart in a tilted position and with support wheel structure positioned for moving the cart from one location to another.

DETAILED DESCRIPTION OF THE PREFERRED EMBODIMENT

Referring initially to FIG. 1 of the drawings, a bottled gas cart 11 in accordance with this example of the invention has a housing 12 forming an internal compartment 13 that is proportioned to contain and enclose two conventional gas bottles or cylinders 14 that are disposed in upright side by side positions. The housing 12 may have an essentially rectangular shape and is greater in height than in width and depth in order to accomodate to the elongated shape of cylinders 14. The housing 12 is preferably formed of steel or other high strength material in order to support and adequately protect the heavy cylinders 14.

The upper portion 17 of the front of housing 12 has a rectangular recess 18 in which a conforming control console panel 19 is disposed and secured. The recess 18 is situated above an outwardly extending step 21 in the front of housing 12 and the recess and control panel 19 are slightly inclined to facilitate viewing of the panel. A transverse rod 22 extends in parallel relationship with the front of housing 12 above control panel 19 and is secured to the housing by brackets 23 situated at each end of the rod. Rod 22 provides a handle which may be grasped to tilt the housing 12 and to travel the cart 11 along the floor or other underlying surface.

To access compartment 13 for installation and removal of cylinders 14 or for other purposes, housing 12 has front and back portions 24 and 26 respectively that are hinged together by hinges 27 which extend vertically along each of the opposite side walls of the housing. Referring jointly to FIGS. 2 and 3, the back portion of the housing 12 is formed by two right angled panel members 28 each of which is hinged to an opposite side of the front portion 24 by a hinge 27. Each panel member 28 is proportioned to define the back region of one of the housing side walls and one half of the back wall of the housing when the housing is in the closed condition. Rectangular top panels 29 are welded to the tops of panel members 28 and jointly form the top wall of the rear portion of the housing 12. Triangular gusset plates 31 are welded to the angled regions of panel members 28 to strengthen the housing and to assure rigidity. For similar reasons, additional gusset plates 32 and 33 are welded to the free edges of each top panel 29 and to the adjacent portions of the free edges of panel members 28.

The floor of housing 12 is formed by a rectangular plate 34 which is secured to the front portion 24 of the housing and which extends backward to provide a platform on which the pair of gas cylinders 14 may be rested and which conforms in outline with the configuration of the hinged panel members 28 when the panel members are swung to the closed position. Referring to FIGS. 2, 3 and 4 in conjunction, the bases of the cylinders 14 are abutted against a rectangular plate 36 which extends upward from the platform plate 34 at the front of the cylinder compartment 13 and an upper region of each cylinder is disposed against a cross brace 37 which extends transversely between the side walls of the front portion of the housing 12 at a location above plate 36. The cylinders 14 also abut a pair of tubular members 38 and 39 which extend rearwardly between the cylinders from plate 36 and cross brace 37 respectively.

The cylinders are secured in place at the above described positions by a clamping bar 41 which spans the two cylinder. A threaded projection 42 at the free end of the upper tubular member 39 extends through a bore at the center of clamping bar 41 and the bar is secured in place by engaging an internally threaded end of a clamp tightening arm 43 on the threaded projection 42. Turning of the arm 43 in one direction forces clamping bar 41 towards the front of housing 12 and thus clamps the cylinders 14 against plate 36 and cross brace 37. Clamping bar 41 has ends 44 which are somewhat angled towards the front of housing 12. This causes the bar 41 to exert a further force which clamps the cylinders against tubular members 38 and 39. Thus the two cylinders 14 are rigidly held at fixed positions within the housing 12 including at times when the housing is tilted and being moved. The cylinders can easily be removed when replacement is needed by turning arm 43 in an opposite direction to disengage the arm from projection 42 after which clamping bar 41 may be temporarily removed from the projection.

The load bearing region at the base of housing 14 is strengthened by three additional vertically oriented triangular gusset plates 46 which extend between the lower region of plate 36 and platform 34, a pair of the gussets being at the opposite side edges of the platform and the other being centered on the platform. The housing 12 is held closed by door latches 47 which are secured to the hinged panel members 28 and which may be of conventional construction.

Referring again to FIGS. 2 and 3 in particular, the above described construction of the housing 12 greatly facilitates installation and removal of the heavy cylinders 14 as panel members 28 can be swung outward to the depicted positions leaving the region of the cylinders virtually unobstructed on three sides and at the top.

Referring to FIG. 5, the cart has a self-contained system 48 of piping and fluid circuit components that enables simultaneous connection of a plurality of surgical tools or other gas consuming devices to a cylinder 14, selection of the gas pressure that is supplied to the tools including simultaneous supplying of different pressures to different tools and switching from one gas cylinder to another by a simple control manipulation.

For this purpose the system 48 includes a three way cylinder selector valve 49 having a gas flow outlet 51 and two inlets 52 and 53 each of which is communicated with the outlet valve 54 of a separate one of the gas cylinders 14. Selector valve 49 has three positions of which one is an off position at which gas flow through the valve is blocked. Inlet 52 is communicated with the outlet 51 at a second of the valve settings and the third setting communicates the other inlet 53 with the outlet. Thus the selector valve 49 enables the operator to start and stop gas delivery by the cart and to switch from a first of the cylinders to the other when pressure in the first cylinder drops below the minimum level that is needed for operation of the surgical tools or the like. First and second pressure gauges 56 and 57 are communicated with the outlet valves 54 of separate ones of the cylinders 14 to enable operator monitoring of the pressures in the two cylinders. Gauges 56 and 57 in this example visually indicate pressure readings up to 3000 psi.

Gas flow from selector valve 49 is transmitted to a pressure reducing pressure regulator 58 which establishes a system pressure that has a maximum value of 300 psi in this particular example of the invention. Regulator 58 is preferably adjustable to enable operator selection of system pressure.

This embodiment of the invention has four gas flow outlet fittings 59 of the known type which release gas only when an intake fitting of a gas delivery hose (not shown) is engaged in the outlet fitting. Gas flow from the system regulator 58 is transmitted to a first group 61 of the outlet fittings 59 through a first group pressure regulator 62 and is transmitted to a second group 63 of the outlet fittings through a second group pressure regulator 64 and enable operator selected further pressure reductions which need not necessarily be the same for the two groups 61 and 63 of outlet fittings 59.

A third pressure gauge 66 is communicated with the outlet of regulator 58 to enable operator monitoring of system pressure. Fourth and fifth pressure gauges 67 and 68 are communicated with the outlet fittings 59 of the first and second groups 61 and 63 respectively to enable operator monitoring of the pressures that are being delivered at each group.

The above described valves 53 and 54, pressure rereducing regulators 58, 62 and 64, fittings 59 and gauges 56, 57, 66, 67 and 68 may each be of conventional design. Referring to FIGS. 1 and 2, the fluid circuit components which can be adjusted by the operator or which have dials or the like that can be visually monitored by the operator are secured to the back of the control panel 19 at openings in the panel that enable viewing of the gauges 56, 57, 66, 67, 68 and manipulation of the actuator 69 of selector valve 49 and the pressure selectors 71 of outlet pressure regulators 62 and 64. Outlet fittings 59 are secured to a vertically oriented bottom portion 72 of the control panel 19 and are also accessible from the front of the cart 11. The system pressure regulator 58 shown in FIG. 2 is secured to the top of the previously described cross brace 37 shown in FIG. 3.

Referring again to FIG. 5, the number of gas flow delivery outlets 59 and groups of such outlets with separate regulators 62, 64 may be varied to accommodate to the needs of different operating rooms or other usage sites.

Referring to FIG. 1 in particular, movement of the cart 11 from one location to another is provided for in part by first and second similar wheels 73 and 74 respectively situated at opposite sides of the cart 11 in front of the base of the front face 76 of housing 12. Wheels 73 and 74 are journalled to a horizontal axle rod 77 which extends in parallel spaced apart relationship with housing face 76 and which is secured in place by brackets 78 that extend outward from opposite sides of the housing face. For reasons to be hereinafter described, wheels 73 and 74 are preferably located to be slightly elevated from the floor or other underlying surface when the housing 12 is in its upright orientation, the wheels being spaced from the floor by one inch in this example.

Referring to FIGS. 1 and 7 in conjunction, the cart 11 is provided with a third wheel 79 carried by linkage means 81 which enables movement of the wheel from a first location adjacent housing face 76 as shown in FIG. 1 to a second location at which the wheel is spaced outwardly from the housing face in position to contact the floor when housing 12 is tilted as shown in FIG. 7. Wheel 79 is attached to the lower end of a pivoting leg 82 by a swivel 83 which enables the wheel to track turns in the motion of the cart 11. Leg 82 extends up into a slot 83 at the center of the step 21 in the front face of housing 12 and is pivoted to the housing by a pivot coupling 84 situated just above the step.

Leg 82, which is of rectangular cross section in this example of the invention, extends through a conforming slider frame 86 which may be traveled along the leg and which enables locking of the leg and thus wheel 79 at both of the first and second locations described above. Travel of slider frame 86 along the frame in response to pivoting of leg 82 is brought about by a pair of angled arms 87 which have first ends pivoted to opposite sides of the slider frame by pivot couplings 88 and opposite ends which pivotably engage the axle rod 77 of the first and second wheels 73 and 74 at locations adjacent brackets 78.

Referring jointly to FIGS. 1 and 6, the slider frame 86 is immobilized relative to leg 82 by entry of a latching pin 89 into either of a pair of apertures 91 and 92 in the leg. The lower aperture 91 is located to be engaged by pin 89 when the leg 82 and third wheel 79 are at the first location adjacent housing 12 and the upper aperture 92 is positioned to be engaged by the pin when the leg and wheel are at the second or extended position.

Slider 86 has a spring chamber 93 through which pin 89 extends and a compression spring 94 within the chamber bears against a flange 96 on the pin to urge the pin in the direction of leg 82. Thus the pin 89 is held in its latching engagement with one of the apertures 91 and 92 until it is manually retracted. An enlarged head 97 on the pin 89 facilitates such unlatching at times when the leg 82 is to be pivoted from one position to the other.

Positioning of leg 82 and wheel 79 at the first location when the cart 11 is in its stationary and upright orientation effects a substantial saving of space in the operating room and increases stability by shifting weight closer to the support base. Positioning of the leg 82 and wheel 79 at the second location provides highly stable support during movement of the cart 11 and frees the operator from any need to exert effort in order to hold the cart in the tilted orientation. The operator is only required to push or pull on the cart.

Tilting of the heavy cart 11 between the upright position and the inclined traveling position requires less operator effort than might be expected owing to the configuration of the cart. The gravity induced force moment that resists the operator's exertion is a function of the horizontal displacement of the center of gravity of the cart 11 from the point about which the cart is being pivoted and is non-existent when the center of gravity is directly over the pivot point. During the initial stage of tilting out of the upright orientation, the cart pivots about the base of the front face 76 of housing 12. The displacement diminishes and momentarily vanishes when the center of gravity is directly over that pivot point. This occurs at an inclination of about 15 20 in the present embodiment. When the first and second wheels 73, 74 contact the floor the point shifts away from housing 12 in the direction of the lean as the cart now pivots about the axle rod 77. Thus the displacement again diminishes and momentarily vanishes at an inclination of about 30° in the present embodiment. The third wheel 79 contacts the floor when the cart 11 reaches an inclination of 45° in this embodiment and the center of gravity is then located above a point which is between the first and second wheels 73, 74 and the third wheel 79 and the cart is stable and self-supporting.

For similar reasons, raising of the cart 11 from the inclined position to the upright orientation requires less operator effort than might be expected during the later stages of the movement. The pivot point shifts from axle rod 77 to a location directly under the front face 76 of housing 12 as the upright orientation is being approached.

The cart 11 has been herein described with reference to use in hospital operating rooms for the purpose of supplying compressed nitrogen gas to pneumatic surgical tools as it is particularly advantageous in this context. Essentially similar carts can be used to supply other gases for other purposes including at non-medical facilities where bottled gases are needed.

While the invention has been described with reference to a single preferred embodiment for purposes of example, many variations and modifications of the cart construction are possible and it is not intended to limit the invention except as defined in the following claims.

I claim:

1. In a movable cart for supporting at least one pressurized gas cylinder, the combination comprising:
   a housing having an interior compartment which is proportioned to receive and contain said gas cylinder, said housing having a lower end with means for journaling wheels thereto and wherein said housing has a front face and opposite side surfaces which extend upward from said lower end thereof,
   means for selectively securing said gas cylinder at a fixed position within said housing,
   means for delivering a flow of gas from said cylinder to a location outside of said housing,
   first and second spaced apart wheels journaled to said lower end of said housing, said wheels being at locations which cause said housing to be raised from the underlying floor or the like and to be supported by said wheels when said housing is in a tilted orientation,
   further including a downwardly extending leg disposed at said front face of said housing substantially midway between said side surfaces thereof, a first pivot coupling connecting an upper end of said leg to said housing, said first pivot coupling being oriented to enable pivoting of a lower end of said leg towards said front face of said housing and outward therefrom, a third wheel located substantially equidistant from said side surfaces of said housing and a swivel connector coupling said third wheel to a lower end of said leg,
   further including a slider member engaged on said leg and being slidable therealong, a pair of arms each having an upper end pivoted to said slider member at opposite sides thereof and each having a lower end pivotably coupled to said housing which arms extend downward and away from said leg when said link is pivoted towards said front face of said housing.

2. In a movable cart for supporting at least one pressurized gas cylinder, the combination comprising:
   a housing having an interior compartment which is proportioned to receive and contain said gas cylinder, said housing having a lower end with means for journaling wheels thereto and wherein said housing has a front face and opposite side surfaces which extend upward from said lower end thereof,
   means for selectively securing said gas cylinder at a fixed position within said housing,
   means for delivering a flow of gas from said cylinder to a location outside of said housing,
   first and second spaced apart wheels journaled to said lower end of said housing, said wheels being at locations which cause said housing to be raised from the underlying floor or the like and to be supported by said wheels when said housing is in a tilted orientation,
   further including a downwardly extending leg disposed at said front face of said housing substantially midway between said side surfaces thereof, a first pivot coupling connecting an upper end of said leg to said housing, said first pivot coupling being oriented to enable pivoting of a lower end of said leg towards said front face of said housing and outward therefrom, a third wheel located substantially equidistant from said side surfaces of said housing and a swivel connector coupling said third wheel to a lower end of said leg,
   wherein said leg has a first aperture situated at the location of said slider member on said leg when said lower end of said leg has been pivoted toward said front face of said housing and has a second aperture situated at the location of said slider member on said leg when said lower end of said leg has been pivoted outward from said front face of said housing, and a movable latch pin carried by said slider member in position for engaging in said apertures.

3. In a movable cart for supporting at least one pressurized gas cylinder, the combination comprising:
   a housing having an interior compartment which is proportioned to receive and contain said gas cylinder, said housing having a lower end with means for journaling wheels thereto and wherein said housing has a front face and opposite side surfaces which extend upward from said lower end thereof,
   means for selectively securing said gas cylinder at a fixed position within said housing,
   means for delivering a flow of gas from said cylinder to a location outside of said housing,
   first and second spaced apart wheels journaled to said lower end of said housing, said wheels being at locations which cause said housing to be raised from the underlying floor or the like and to be supported by said wheels when said housing is in a tilted orientation,
   wherein said housing is proportioned to receive a pair of said gas cylinders in upright side by side relationship and has a floor and a front region and opposite side walls and a rear wall which extend upward from said lower end of said housing, said rear wall and at least a rearward portion of each side wall being formed by a pair of angled wall members which are separately hinged to said front region of said housing whereby said wall members may be pivoted away from each other to open said housing for installation and removal of said cylinders.

4. A movable cart for supporting and transporting pressurized gas cylinders comprising:
   a closed housing having a floor, a front wall, opposite site side walls, a rear wall and a top wall forming a compartment of sufficient size to contain a pair of said gas cylinders in upright side by side positions, a first portion of said walls being joined to another portion of said walls by hinges to enable opening of said housing;
   first and second wheels journaled to said housing, said first and second wheels being disposed at opposite side regions of said housing adjacent the base of said front wall thereof and being positioned to extend forward from said base of said front wall and to extend upward from the plane of said floor at locations which cause said housing to be raised from the underlying surface and to be supported by said first and second wheels when said housing is tilted into an inclined orientation and which cause said housing to rest on said underlying surface when said housing is shifted to a more upright orientation;
   at least one pivotable leg disposed adjacent said front wall of said housing, said leg having an upper end that is pivoted to said housing and a lower end that may be pivoted outward from said front wall of said housing;
   means for selectively holding said leg at the outwardly pivoted position of the leg;
   a third wheel coupled to said lower end of said leg and being swivelable relative thereto;
   a plurality of gas outlet fittings secured to said housing and being accessible from outside said housing;
   a cylinder selector valve secured to said housing and having a manually operable valve setting selector that is accessible from outside said housing; and
   means for transmitting gas from a selected one of said gas cylinders to said outlet fittings in response to actuation of said valve setting selector.

* * * * *